US010246409B2

(12) United States Patent
Schnider et al.

(10) Patent No.: US 10,246,409 B2
(45) Date of Patent: Apr. 2, 2019

(54) METHOD FOR PREPARATION OF BIS(FLUOROSULFONYL)-IMIDE

(71) Applicant: Lonza Ltd, Visp (CH)

(72) Inventors: Christian Schnider, Visp (CH); Anna-Christina Hormes, Visp (CH); Andreas Klein, Brig-Glis (CH); Michael Bersier, Ausserberg (CH); Philipp Studer, Visp (CH); Stefan Tille, Naters (CH); Thomas Gruetzner, Thun (CH)

(73) Assignee: Lonza Ltd, Visp (CH)

( * ) Notice: Subject to any disclaimer, the term of this patent is extended or adjusted under 35 U.S.C. 154(b) by 0 days.

(21) Appl. No.: 15/571,524

(22) PCT Filed: May 4, 2016

(86) PCT No.: PCT/EP2016/059965
§ 371 (c)(1),
(2) Date: Nov. 3, 2017

(87) PCT Pub. No.: WO2016/177765
PCT Pub. Date: Nov. 10, 2016

(65) Prior Publication Data
US 2018/0141901 A1 May 24, 2018

Related U.S. Application Data

(60) Provisional application No. 62/157,714, filed on May 6, 2015.

(30) Foreign Application Priority Data

| May 6, 2015 | (EP) | 15166595 |
| May 7, 2015 | (EP) | 15166814 |
| May 9, 2015 | (EP) | 15167048 |
| Nov. 9, 2015 | (EP) | 15193625 |
| Nov. 13, 2015 | (EP) | 15194509 |
| Mar. 15, 2016 | (EP) | 16160244 |
| Mar. 30, 2016 | (EP) | 16163042 |
| Apr. 7, 2016 | (EP) | 16164145 |
| Apr. 8, 2016 | (EP) | 16164370 |
| Apr. 11, 2016 | (EP) | 16164592 |
| Apr. 29, 2016 | (EP) | 16167616 |

(51) Int. Cl.
| B01J 19/00 | (2006.01) |
| C01B 21/086 | (2006.01) |
| C07C 303/36 | (2006.01) |
| C07C 303/40 | (2006.01) |
| C07C 311/48 | (2006.01) |

(52) U.S. Cl.
CPC ........ *C07C 303/40* (2013.01); *B01J 19/0013* (2013.01); *C01B 21/086* (2013.01); *C07C 303/36* (2013.01); *C07C 311/48* (2013.01); *B01J 2219/00029* (2013.01); *B01J 2219/00051* (2013.01); *B01J 2219/00162* (2013.01)

(58) Field of Classification Search
None
See application file for complete search history.

(56) References Cited

U.S. PATENT DOCUMENTS

| 7,919,629 | B2 | 4/2011 | Michot |
| 8,722,005 | B1 | 5/2014 | Poshusta et al. |
| 9,546,136 | B2 | 1/2017 | Schnider et al. |
| 9,725,318 | B2 | 8/2017 | Audureau et al. |
| 2009/0292105 | A1* | 11/2009 | Michot ............... C07D 249/12 528/391 |
| 2011/0034716 | A1* | 2/2011 | Okumura ............. C07C 303/40 556/69 |
| 2015/0246812 | A1 | 9/2015 | Audureau et al. |

FOREIGN PATENT DOCUMENTS

| WO | WO 2009/123328 | 10/2009 |
| WO | WO 2015/004220 | 1/2015 |
| WO | WO 2015/012897 | 1/2015 |

OTHER PUBLICATIONS

PCT/EP2016/059965, International Search Report and Written Opinion, dated Jul. 11, 2016, 10 pages.
PCT/EP2016/059965, International Preliminary Report on Patentability, dated Jul. 21, 2017, 5 pages.

* cited by examiner

*Primary Examiner* — Amy C Bonaparte
(74) *Attorney, Agent, or Firm* — Dority & Manning, P.A.

(57) ABSTRACT

The invention relates to a method for the preparation of bis(fluorosulfonyl)-imide and its derivatives at elevated temperature.

15 Claims, No Drawings

METHOD FOR PREPARATION OF BIS(FLUOROSULFONYL)-IMIDE

CROSS REFERENCE TO RELATED APPLICATIONS

This application is the U.S. National Stage entry of International Application Number PCT/EP2016/059965 filed under the Patent Cooperation Treaty and having a filing date of May 4, 2016, which claims the filing benefit of U.S. Provisional Application No. 62/157,714 having a filing date of May 6, 2015, European Patent Application No. 15166595.7, having a filing date of May 6, 2015, European Patent Application No. 15166814.2, having a filing date of May 7, 2015, European Patent Application No. 15167048.6, having a filing date of May 9, 2015, European Patent Application No. 15193625.9, having a filing date of Nov. 9, 2015, European Patent Application No. 15194509.4, having a filing date of Nov. 13, 2015, European Patent Application No. 16160244.6, having a filing date of Mar. 15, 2016, European Patent Application No. 16163042.1, having a filing date of Mar. 30, 2016, European Patent Application No. 16164145.1, having a filing date of Apr. 7, 2016, European Patent Application No. 16164370.5, having a filing date of Apr. 8, 2016, European Patent Application No. 16164592.4, having a filing date of Apr. 11, 2016 and European Patent Application No. 16167616.8, having a filing date of Apr. 29, 2016, all of which are incorporated herein by reference in their entirety.

FIELD OF THE INVENTION

The invention relates to a method for the preparation of bis(fluorosulfonyl)-imide and its derivatives at elevated temperature.

BACKGROUND OF THE INVENTION

In the following text, the following meanings are used, if not otherwise stated:
ACN acetonitrile;
ClSI bis(chlorosulfonyl)-imide, that is compound of formula (2);

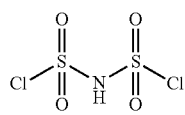

CSI chlorosulfonyl isocyanate, that is compound of formula (3);

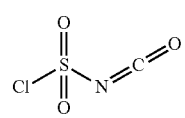

CSOS, CSA chlorosulfonic acid;
DCB dichlorobenzene, if not otherwise stated it is 1,2-dichlorobenzene;
DCE dichloroethane, if not otherwise stated it is 1,2-dichloroethane;
DCM dichloromethane;
DFACl difluoro acetic acid chloride;
DFAF difluoro acetic acid fluoride;
halogen F, Cl, Br or L preferably F, Cl or Br, more preferably F or Cl.
HFSI bis(fluorosulfonyl)-imide, that is compound of formula (1);

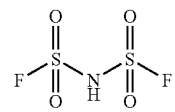

LiFSI Lithium bis(fluorosulfonyl)-imide, that is compound of formula (4);

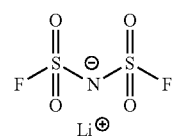

TEA triethylamine;
TFACl trifluoro acetic acid chloride;
TFAF trifluoro acetic acid fluoride;
VN valeronitrile;
wt %, % by weight percent by weight.

HFSI is an intermediate used for the production of electrolytes in electrochemical devices such as in lithium ion batteries in form of its lithium salt LiFSI.

WO 2009/123328 A1 discloses a method for preparation of metal salts of symmetrical and asymmetrical fluorosulfonylimide in a solvent by a reaction of a respective symmetrical or asymmetrical chlorosulfonylimide with a fluoride compound containing at least one element selected from the group consisting of elements of Group 11 to Group 15 and Period 4 to Period 6 (excluding arsenic and antimony), these metal salts are then converted in a second step to salts of various amines and symmetrical and asymmetrical fluorosulfonylimide in a cation exchange reaction.

US 2015/0246812 A1 discloses a method for the preparation of symmetrical and asymmetrical flourosulfonylimides from symmetrical and asymmetrical chlorosulfonylimides, wherein the reaction is done in an organic solvent.

WO 2015/012897 A1 discloses a method for producing FSI from ClSI using HF, wherein the HCl that is produced by the reaction is selectively removed during the reaction to produce HFSI in at least 80% yield. The reaction takes place at ambient (e.g. atmospheric) pressure. Reaction times are much longer than 3 hours. Both requirements, the rather long reaction times and the requirement for separating HCl from the reaction mixture during the reaction, require a special continuous stirred-tank reactor ("CSTR") set-up with a device for the required separation of HCl during the reaction when carrying out the reaction in a continuous way. To do the reaction in a simple continuously working tube shaped reactor creates problems.

Also disclosed is the exchange of Br and I instead of Cl against F, that is the conversion of hydrogen bis(halosulfonyl)imide (HXSI) with hydrogen fluoride for producing hydrogen bis(fluorosulfonyl)imide (HFSI), where each X is independently a nonfluoro-halide, such as Cl, Br, or I.

WO 2015/004220 A1 discloses a method for the preparation of imidodisulfuryl compounds in a continuous reaction at elevated temperatures.

U.S. Pat. No. 7,919,629 B2 discloses in Example 10 the reaction of distilled ClSI with HF and reports i.a. 55% yield for the example with 2 h at 130° C.

There was a need for a method for preparation of HFSI that does not require mandatorily a solvent, that does not require mandatorily metal salts, and that has few steps, that produces HFSI in high yields and in that can done both batch wise and in a continuous manner in a continuous reactor, and also and a continuous tube shape reactor.

The method should not require the separation of HCl during the reaction for enhancement of the yield, as it is disclosed in WO 2015/012897 A1 and should allow to carry out the reaction in relatively short reaction times.

Unexpectedly a method for preparation of HFSI was found starting from ClSI, that does not require a solvent, that does not require metal salts, that has few steps, that produces HFSI in high yields in spite of the poor solubility and miscibility of HF in ClSI and vice versa, and that can be done both batch wise or in a continuous manner and also in a continuous tube shape reactor, and that is distinguished by short reaction times.

Unexpectedly, the method does not require the separation of HCl during the reaction, which is formed by the reaction, and still provides HFSI in good yields. This was unexpected in view of the disclosure of WO 2015/012897 A1. Furthermore it was unexpected that the use of a mixture comprising ClSI, CSI and chlorosulfonic acid in the reaction with HF provides for significantly higher yield than the use of ClSI alone as disclosed in U.S. Pat. No. 7,919,629 B2. This is exemplified herein with Comparative Example (i) versus Example 7.

The reaction can be done with relatively short reaction times compared to the disclosure in the prior art, which allows to do the reaction not only batch wise, but also in continuous manner, also in a continuous tube shape reactor.

SUMMARY OF THE INVENTION

Subject of the invention is a method for preparation of compound of formula (I):

$$\underset{F}{\overset{O}{\underset{\|}{\overset{\|}{S}}}}\underset{O}{\overset{}{\underset{H}{N}}}\underset{O}{\overset{O}{\underset{\|}{\overset{\|}{S}}}}X \quad (I)$$

the method comprises a step STEP1;
STEP1 comprises a reaction REAC1-1;
in REAC1-1 a mixture MIXTURE-TRIPLE is reacted with HF
at a temperature TEMP1-1, TEMP1-1 is at least 80° C.;
MIXTURE-TRIPLE comprises three components, a compound of formula (II), a compound of formula (III) and a compound of formula (IV);

$$X1\underset{O}{\overset{O}{\underset{\|}{\overset{\|}{S}}}}\underset{H}{\overset{}{N}}\underset{O}{\overset{O}{\underset{\|}{\overset{\|}{S}}}}X2 \quad (II)$$

$$X1\underset{O}{\overset{O}{\underset{\|}{\overset{\|}{S}}}}N=C=O \quad (III)$$

$$R^{n+}\left[\underset{O}{\overset{O}{\underset{\|}{\overset{\|}{S}}}}X2\right]_n \quad (IV)$$

X is identical with X1 or with X2;
X1 and X2 are identical or different and independently from each other selected from the group consisting of F, Cl, Br, I, RESF, and tolyl;
RESF is fluorinated $C_{1-9}$ alkyl, which is unsubstituted or substituted by a substituent $OCF_3$;
$R^{n+}$ is selected from the group consisting of $H^+$, $Li^+$, $Na^+$, $K^+$, $Mg^{2+}$, $Ca^{2+}$, $Zn^{2+}$, $Cu^{2+}$, $Al^{3+}$, $Ti^{3+}$, $Fe^{2+}$, $Fe^{3+}$, $B^{3+}$,

[structures of imidazolium with R21, R20; pyrrolidinium with R20, R21; pyridinium with R20; piperidinium with R20, R21]

$[N(R20)(R21)(R22)R23]^+$, and $[P(R20)(R21)(R22)R23]^+$;
R20, R21, R22 and R23 are identical or different and independently from each other selected from the group consisting of H, $C_{1-8}$ alkyl, $C_{5-6}$ cycloalkyl, phenyl, benzyl, vinyl and allyl;
n is 1, 2 or 3;
wherein
the total content of the three components in MIXTURE-TRIPLE is of from 50 to 100%, the % being % by weight based on the total weight of MIXTURE-TRIPLE;
wherein
the relative ratio of the three components in MIXTURE-TRIPLE is of from
  2 to 98% of compound of formula (II),
  49 to 1% of compound of formula (III), and
  49 to 1% of compound of formula (IV);
the % are % by weight and are based on the combined weight of the three components in MIXTURE-TRIPLE; the relative ratios of the three components add up to 100%.

DETAILED DESCRIPTION OF THE INVENTION

The expression "X is identical with X1 or with X2" means that either X stems from compound of formula (III), that means X is X1, or X stems from compound of formula (IV), that means X is X2.

Preferably, X is identical with X2, that means X stems from compound of formula (IV).

"Fluorinated alkyl" means, that at least one H is exchanged for F.

Preferably,
  RESF is fluorinated $C_{1-6}$ alkyl, which is unsubstituted or substituted by a substituent $OCF_3$;

more preferably,
RESF is fluorinated $C_{1-4}$ alkyl, which is unsubstituted or substituted by a substituent $OCF_3$;
even more preferably.
RESF is fluorinated $C_{1-2}$ alkyl, which is unsubstituted or substituted by a substituent $OCF_3$.

Especially, any RESF herein is a perfluoroalkyl.

Specific embodiments of RESF are for example $CF_3$, $CHF_2$, $CH_2F$, $C_2F_5$, $C_2HF_4$, $C_2H_2F_3$, $C_2H_3F_2$, $C_2H_4F$, $C_3F_7$, $C_3HF_6$, $C_3H_2F_5$, $C_3H_4F_3$, $C_3H_6F$, $C_4F_9$, $C_4H_2F_7$, $C_4H_4$, $F_5$, $C_4H_8F$, $C_5F_{11}$, $C_5H_{10}F$, $C_3F_5OCF_3$, $C_2F_4OCF_3$, $C_2H_2F_2OCF_3$, $CF_2OCF_3$, $C_6F_{13}$, $C_6H_{12}F$, $C_7F_{15}$, $C_8F_{17}$ and $C_9F_{19}$;
preferably $CF_3$, $CHF_2$, $CH_2F$, fluoroethyl, difluoroethyl, 2,2,2-trifluoroethyl, pentafluoroethyl, 3,3,3-trifluoropropyl, a perfluoro-n-propyl, fluoropropyl, perfluoroisopropyl, fluorobutyl, 3,3,4,4,4-pentafluorobutyl, perfluoro-n-butyl, perfluoroisobutyl, perfluoro-t-butyl, perfluoro-sec-butyl, fluoropentyl, perfluoropentyl, perfluoroisopentyl, perfluoro-t-pentyl, fluorohexyl, perfluoro-n-hexyl and perfluoroisohexyl;
more preferably, trifluoromethyl, pentafluoroethyl and perfluoro-n-propyl;
even more preferably, trifluoromethyl and pentafluoroethyl.

Preferably,
X1 and X2 are identical or different and independently from each other selected from the group consisting of F, Cl, Br, I, RESF, RESF being preferably $C_{1-6}$ perfluoroalkyl, and tolyl;
$R''^+$ is selected from the group consisting of $H^+$, $Li^+$, $Na^+$, $K^+$, $Mg^{2+}$, $Ca^{2+}$, $Zn^{2+}$, $Cu^{2+}$, $Al^{3+}$, $Ti^{3+}$, $Fe^{2+}$, $Fe^{3+}$, $B^{3+}$,

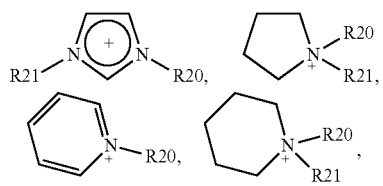

$[N(R20)(R21)(R22)R23]^+$, and $[P(R20)(R21)(R22)R23]^+$;
R20, R21, R22 and R23 are identical or different and independently from each other selected from the group consisting of H, $C_{1-8}$ alkyl, $C_{5-6}$ cycloalkyl, phenyl, benzyl, vinyl and allyl;
n is 1, 2 or 3.

More preferably,
X1 and X2 are identical or different and independently from each other selected from the group consisting of F, Cl, Br, RESF, RESF being preferably $C_{1-6}$ perfluoroalkyl, and tolyl;
$R''^+$ is selected from the group consisting of $H^+$, $Li^+$, $Na^+$, $K^+$, $Mg^{2+}$, $Al^{3+}$,

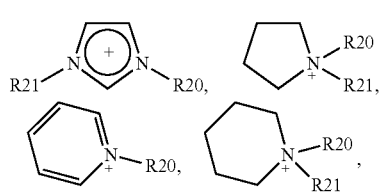

and $[N(R20)(R21)(R22)R23]^+$;
R20, R21, R22 and R23 are identical or different and independently from each other selected from the group consisting of H, $C_{1-4}$ alkyl, phenyl, benzyl, vinyl and allyl;
n is 1, 2 or 3.

Even more preferably,
X1 and X2 are identical or different and independently from each other selected from the group consisting of F, Cl, and RESF, RESF being preferably $C_{1-4}$ perfluoroalkyl;
$R''^+$ is selected from the group consisting or $H^+$, $Li^+$, $Na^+$,

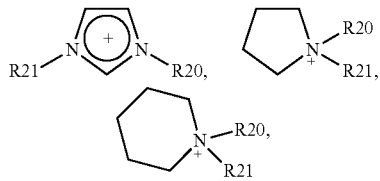

and $[N(R20)(R21)(R22)R23]^+$;
R20, R21, R22 and R23 are identical or different and independently from each other selected from the group consisting of H, and $C_{1-4}$ alkyl;
n is 1.

Especially,
X1 and X2 are identical or different and independently from each other selected from the group consisting of Cl, and RESF, RESF being preferably $C_{1-2}$ perfluoroalkyl;
$R''^+$ is selected from the group consisting of $H^+$, $Li^+$, $Na^+$,

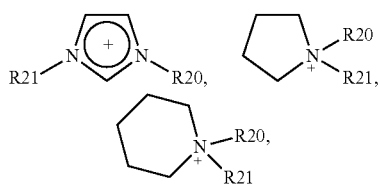

and $[N(R20)(R21)(R22)R23]^+$;
R20, R21, R22 and R23 are identical or different and independently from each other $C_{1-4}$ alkyl;
n is 1.

More especially,
X1 and X2 are identical or different and independently from each Cl or $CF_3$;
$R''^+$ is selected from the group consisting of $H^+$, $Li^+$, and $Na^+$;
n is 1.

Even more especially,
X1 and X2 are identical or different and independently from each Cl or $CF_3$;
$R''^+$ is $H^+$;
n is 1.

Specific embodiments of compound of formula (I) are compound of formula (1) and compound of formula (1-CF3).

(1-CF3)

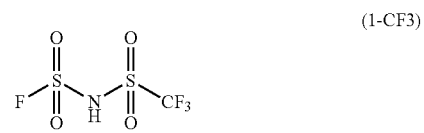 [SMILES: O=S(=O)(F)NS(=O)(=O)C(F)(F)F]

Specific embodiments of compound of formula (II) are compound of formula (2) and compound of formula (2-CF3).

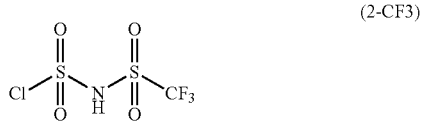 [SMILES: O=S(=O)(Cl)NS(=O)(=O)C(F)(F)F]

(2-CF3)

Specific embodiments of compound of formula (IV) are chlorosulfonic acid and trifluoromethyl sulfonic acid.

In one particular embodiment,
compound of formula (I) is compound of formula (1),
compound of formula (II) is compound of formula (2),
compound of formula (III) is compound of formula (3),
and compound of formula (IV) is chlorosulfonic acid,
that means X, X1 and X2 are Cl, $R^{n+}$ is $H^+$ and n is 1.

In another particular embodiment,
compound of formula (I) is compound of formula (1-CF3),
compound of formula (II) is compound of formula (2-CF3),
compound of formula (III) is compound of formula (3),
and compound of formula (IV) is trifluoromethyl sulfonic acid,
that means X1 is Cl, $R^{n+}$ is $H^+$, and X and X2 are $CF_3$, and n is 1.

Preferably, REAC1-1 is done at a pressure PRESSURE1-1.

Preferably, PRESSURE1-1 is at least ambient pressure, more preferably at least 2 bar, even more preferably at least 5 bar, very even more preferably at least 10 bar, very, very even more preferably at least 20 bar, especially at least 30 bar, more especially at least 40 bar, even more especially at least 45 bar, very even more especially at least 50 bar, very, very even more especially at least 55 bar, in particular at least 60 bar, more in particular at least 65 bar, even more in particular at least 70 bar, very even more in particular at least 75 bar, very, very even more in particular at least 80 bar.

The upper limit of the pressure is mainly determined by the devices and their ability to provide and/or stand the pressure. Purely out of such considerations and without limiting the invention, PRESSURE1-1 is preferably up to 1000 bar, more preferably up to 750 bar, even more preferably up to 600 bar, especially up to 500 bar.

Any of the lower limits of PRESSURE1-1 can be combined with any of the upper limits of PRESSURE1-1; preferably, PRESSURE1-1 is from ambient pressure to 1000 bar, more preferably from 2 to 1000 bar, even more preferably from 5 to 1000 bar, very even more preferably from 10 to 1000 bar, very, very even more preferably from 20 to 1000 bar, especially from 30 to 1000 bar, more especially from 40 to 1000 bar, even more especially from 45 to 1000 bar, very even more especially from 50 to 1000 bar, in particular from 55 to 1000 bar, more in particular from 60 to 1000 bar, even more in particular from 65 to 1000 bar, very even more in particular from 70 to 750 bar, very, very even more in particular from 75 to 600 bar, 3 times very even more in particular from 80 to 500 bar.

Preferably, TEMP1-1 is at least 80° C., more preferably at least 90° C., even more preferably at least 100° C., especially at least 110° C., more especially at least 120° C., even more especially at least 125° C., in particular at least 130° C., more in particular at least 135° C., even more in particular at least 140° C., very even more in particular at least 145° C., very, very even more in particular at least 150° C., very, very, very even more in particular at least 155° C., very, very, very, very even more in particular at least 160° C.

The upper limit of the temperature is mainly determined by the residence time of the components at elevated temperatures, the shorter the residence time the higher can be the temperature; and also be the resistance against corrosion of the chosen materials of the devices at elevated temperatures. Purely out of such considerations and without limiting the invention, TEMP1-1 can preferably be up to 300° C., more preferably up to 290° C., even more preferably up to 280° C., especially up to 270° C., more especially up to 260° C., even more especially up to 250° C., in particular up to 240° C., more in particular up to 230° C.

Preferably, TEMP1-1 is from 80 to 300° C., more preferably from 90 to 300° C., 100 to 300° C., even more preferably from 110 to 290° C., especially from 120 to 280° C., more especially from 130 to 280° C., even more especially from 130 to 280° C., in particular from 140 to 280° C., more in particular from 145 to 280° C., even more in particular from 150 to 250° C., very even more in particular from 150 to 230° C., very, very even more in particular from 155 to 230° C.

Any of the given minimum points, maximum points and/or ranges of TEMP1-1 can be combined with any of the given minimum points, maximum points and/or ranges of PRESSURE1-1.

Preferably, mixture of MIXTURE-TRIPLE and HF is heated in a device DEVICE1-1 to TEMP1-1, REAC1-1 takes place in DEVICE1-1.

Preferably, TIME1-1 is the time, where the mixture is exposed to heating, preferably to TEMP1-1, preferably in DEVICE1-1. During TIME1-1 REAC1-1 takes place. TIME1-1 is therefore preferably a residence time and is preferably the residence time of the mixture in DEVICE1-1.

Preferably, TIME1-1 is from 1 min to 2 h, more preferably from 2 min to 1.5 h. even more preferably 5 min to 1 h, especially from 5 min to 30 min.

Preferably, HCl, that is produced in REAC1-1, is not removed selectively during REAC1-1 to produce compound of formula (I) in at least 80% yield;
more preferably, HCl, that is produced in REAC1-1, is not removed selectively during REAC1-1 to produce compound of formula (I) in higher yield;
even more preferably, HCl, that is produced in REAC1-1, is not removed selectively during REAC1-1.

In another preferred embodiment, HCl, that is produced in REAC1-1, is not removed selectively to produce compound of formula (I) in at least 80% yield;
more preferably, HCl, that is produced in REAC1-1, is not removed selectively to produce compound of formula (I) in higher yield;
even more preferably, HCl, that is produced in REAC1-1, is not removed selectively.

MIXTURE-TRIPLE can be prepared according to known methods, for example by mixing the three components, Other components in MIXTURE-TRIPLE besides the three components compound of formula (II), compound of formula (III), and compound of formula (IV), can be e.g. a solvent. Such a solvent can be any solvent that is inert against the three components of MIXTURE-TRIPLE and against HF. Examples for such solvents are disclosed in US 2015/0246812 A1. As organic solvent, mention may in particular be made of esters, nitriles or dinitriles, ethers or diethers, amines or phosphines, such as for example methyl acetate, ethyl acetate, butyl acetate, acetonitrile, propionitrile, isobutyronitrile, glutaronitrile, dioxane, tetrahydrofuran, methyl tetrahydrofuran, triethylamine, tripropylamine, diethylisopropylamine, pyridine, trimethylphosphine, triethylphosphine and diethylisopropylphosphine, preferably ethyl acetate, butyl acetate, acetonitrile, dioxane, tetrahydrofuran and methyl tetrahydrofuran.

Preferably, the total content of the three components in MIXTURE-TRIPLE is of from 75 to 100%, more preferably of from 90 to 100%, even more preferably of from 95 to 100%, especially of from 97.5 to 100%, more especially of from 98 to 100%, the % being % by weight based on the total weight of MIXTURE-TRIPLE.

In a preferred embodiment, MIXTURE-TRIPLE comprises the three components, compound of formula (II), compound of formula (III) and compound of formula (IV).

In another preferred embodiment, MIXTURE-TRIPLE consists essentially of the three components compound of formula (II), compound of formula (III), and compound of formula (IV).

In another preferred embodiment, the relative ratio of the three components in MIXTURE-TRIPLE is of from
2 to 96% of compound of formula (II),
49 to 2% of compound of formula (III), and
49 to 2% of compound of formula (IV);
more preferably of from
50 to 96% of compound of formula (II),
25 to 2% of compound of formula (III), and
25 to 2% of compound of formula (IV);
even more preferably of from
70 to 96% of compound of formula (II),
15 to 2% of compound of formula (III), and
15 to 2% of compound of formula (IV);
especially of from
75 to 96% of compound of formula (II),
12.5 to 2% of compound of formula (III), and
12.5 to 2% of compound of formula (IV);
more especially of from
75 to 94% of compound of formula (II),
12.5 to 3% of compound of formula (III), and
12.5 to 3% of compound of formula (IV);
even more especially of from
75 to 92% of compound of formula (II),
12.5 to 4% of compound of formula (III), and
12.5 to 4% of compound of formula (IV);
the % are % by weight and are based on the combined weight of the three components in MIXTURE-TRIPLE; the relative ratios of the three components add up to 100%.

Preferably, the molar amount of HF is from 2 to 40 times, more preferably from 2 to 20 times, and even more preferably from 2 to 12.5 times, especially from 2 to 10 times, more especially from 2 to 5 times, even more especially from 2 to 4 times, in particular from 2 to 3 times, more in particular from 2 to 2.5 times, based on the molar amount of compound of formula (II).

In principle it is also possible to use the HF in substoichiometric amounts, that is below 2 equivalents, with respect to the molar amount of compound of formula (II). Naturally in such a case the yield will be lower with respect to compound of formula (II). But also this embodiment is comprised by the invention. Therefore also preferably, the molar amount of HF is from 0.1 to 40 times, more preferably from 0.2 to 40 times, and even more preferably from 0.5 to 40 times, especially 1 to 40 times, more especially 1.5 to 40 times, even more especially 1.75 to 40 times, based on the molar amount of compound of formula (II).

Preferably, at least one of the residues X1 and X2 is Cl, Br, or I, more preferably Cl or Br, even more preferably Cl.

Preferably, the lower limit LOWLIMIT of the amount of HF is 1 equivalent based on the molar amount of compound of formula (II) in case that only one of the residues X1 and X2 is Cl, Br, or J;

LOWLIMIT is 2 equivalents in case that both residues X1 and X2 are identical or different and selected from the group consisting of Cl, Br, and J.

Preferably, the molar amount of HF is from LOWLIMIT to 40 times, more preferably from LOWLIMIT to 20 times, and even more preferably from LOWLIMIT to 12.5 times, especially from LOWLIMIT to 10 times, more especially from LOWLIMIT to 5 times, even more especially from LOWLIMIT to 4 times, in particular from LOWLIMIT to 3 times, more in particular from LOWLIMIT to 2.5 times, based on the molar amount of compound of formula (II).

In principle it is also possible to use the HF in substoichiometric amounts, that is below LOWLIMIT, with respect to the molar amount of compound of formula (II). Naturally in such a case the yield will be lower with respect to compound of formula (II). But also this embodiment is comprised by the invention. Therefore also preferably, the molar amount of HF is from 0.1 to 40 times, more preferably from 0.2 to 40 times, and even more preferably from 0.5 to 40 times, especially 1 to 40 times, more especially 1.5 to 40 times, even more especially 1.75 to 40 times, of LOWLIMIT, based on the molar amount of compound of formula (II).

Any of these lower ranges can be combined with any of the upper ranges given herein and vice versa.

Preferably, REAC1-1 is done in a continuous way.

In a preferred embodiment, STEP1 comprises two consecutive steps, a step STEP1-1 and a step STEP1-3;
in STEP1-1 a mixture MIXTURE1-1, MIXTURE1-1 is a mixture of MIXTURE-TRIPLE and HF, is heated in a device DEVICE1-1 to TEMP1-1, REAC1-1 takes place in DEVICE1-1 resulting in a reaction mixture,
in STEP1-3 the reaction mixture from DEVICE1-1 passes through a device DEVICE1-3, DEVICE1-3 is a device for back pressure regulation.

Preferably, STEP1 comprises a third step, a STEP1-2, which is done either before or after STEP1-3, preferably between STEP1-1 and STEP1-3, in STEP1-2 the reaction mixture from DEVICE1-1 passes through a device DEVICE1-2, DEVICE1-2 is a device for cooling the reaction mixture.

Preferably, the reaction mixture is cooled by the effects of DEVICE1-2 or of DEVICE1-3 or of a combination of DEVICE1-2 and DEVICE1-3 on the reaction mixture.

DEVICE1-1, DEVICE1-2 and DEVICE1-3 are continuously working devices.

Time TIME1-2 is a time, where the reaction mixture is cooled, preferably to TEMP1-2. Preferably, the cooling can be done by the action of DEVICE1-2, by the action of DEVICE1-3 or by the action of DEVICE1-2 and DEVICE1-3. TIME1-2 is therefore preferably a residence time and is preferably the residence time of the reaction mixture in DEVICE1-2 and/or in DEVICE1-3.

Preferably, TIME1-2 is from 0.1 sec to 2 h. more preferably from 0.5 sec to 1 h, even more preferably 1 sec to 30 min, especially from 10 sec to 30 min, more especially from 25 sec to 25 min, even more especially from 1 min to 25 min.

The cooling in STEP1-2 is preferably done to a temperature TEMP1-2, preferably, TEMP1-2 is from 0 to 150° C., more preferably from 10 to 100° C., even more preferably from 10 to 50° C., especially from 15 to 40° C. more especially from 15 to 30° C.

Preferably, the method comprises furthermore a step STEP1-4, STEP1-4 is done after STEP1-3, in STEP1-4 the reaction mixture from DEVICE1-3 passes through a device DEVICE1-4, DEVICE1-4 is a device for separating gaseous components from liquid components in the reaction mixture.

The byproduct of REAC1-1 is HCl.

Preferably, MIXTURE1-1 is fed into DEVICE0-1, during the passage through DEVICE1-1, the initially fed MIXTURE1-1 gradually is converted to the reaction mixture by REAC1-1.

Preferably, DEVICE1-1 is selected from the group consisting of tube, microreactor, shell and tube heat exchanger, plate heat, exchanger and any common device which purpose is to exchange heat from a fluid;
more preferably it is a tube;
even more preferably it is a coiled tube.

Preferably, DEVICE1-2 is selected from the group consisting of tube, microreactor, shell and tube heat exchanger, plate heat exchanger and any common device which purpose is to exchange heat from a reaction mixture;
more preferably it is a tube;
even more preferably it is a coiled tube.

Especially, DEVICE1-1 and DEVICE1-2 are coiled tubes.

Preferably, DEVICE1-3 is a conventional back pressure regulating device.

Preferably, DEVICE1-4 a device capable of separating gaseous components from a liquid, any known device suitable for this purpose for can be used for this purpose, more preferably DEVICE1-4 is a vessel, a column or a cyclone.

The heating, preferably in DEVICE1-1, can be done be any known means, preferably it is done by electric heating or by heating with a fluid heat carrier.

Cooling, preferably in DEVICE1-2, can be done be any known means, preferably it is done by a fluid cooling medium.

Depending on the scale of the reaction and thereby on the scale of the apparatus, wherein the method is done, the cooling of the reaction mixture is done not only by the effect of DEVICE1-2 on the reaction mixture, i.e. it is not only during the passage of the reaction mixture through DEVICE1-2, but additionally the effects of DEVICE1-3 on the reaction mixture, i.e. the passage through DEVICE1-3 contributes to the cooling. This is especially the case when the scale of the reaction is rather small, e.g. when the method is done on lab scale, whereas in case where the method is done on a production scale the cooling will usually primarily be done during the passage through DEVICE1-2.

In another embodiment, especially on production scale, cooling can also be achieved by the expansion and pressure release affected by DEVICE1-3.

Also a combination of cooling during the passage through DEVICE1-2 with a cooling by expansion effected by DEVICE1-3 is possible.

Therefore when the description refers to a cooling in DEVICE1-2, this reference also comprises cooling in DEVICE1-3 and cooling in both devices DEVICE1-2 and DEVICE1-3.

Preferably, heating in DEVICE1-1 and cooling in DEVICE1-2 is realized in form of a tube-in-tube set up, in form of a tube-in-container set up, in form of a shell and tube heat exchanger, plate heat exchanger or any common device which purpose is to exchange heat from a mixture or a reaction mixture;
more preferably, heating in DEVICE1-1 and cooling in DEVICE1-2 is realized in form of a tube-in-tube set up or in form of a tube-in-container set up.

REAC1-1 is triggered, preferably in DEVICE1-1, by the heating of the mixture to TEMP1-1, preferably in the DEVICE1-1.

The PRESSURE1-1 in DEVICE1-1 and preferably in DEVICE1-2 is controlled and maintained by the DEVICE1-3.

HF and MIXTURE-TRIPLE can be fed into the DEVICE1-1 as a premixed mixture or can be fed into the DEVICE1-1 separately and are mixed in DEVICE1-1.

For the purpose of mixing of HF and MIXTURE-TRIPLE before or in DEVICE1-1 any suitable installation for mixing can be used, which are known in the state of the art, such as a common branch connection, e.g. a T or Y piece, or a static mixing device.

Preferably the heating to TEMP1-1 in DEVICE1-1 is done only when both HF and MIXTURE-TRIPLE are present in DEVICE1-1.

The feeding of HF and MIXTURE-TRIPLE, either separately or in form of a mixture, is done by a device DEVICE1-0.

DEVICE1-0 is a pressuring device conventionally used to convey a fluid against pressure, such as a pump. When HF and MIXTURE-TRIPLE are fed separately into DEVICE1-1, then preferably DEVICE1-0 has for each component reagent a respective device; a device DEVICE1-0-HF for conveying the HF, and a device DEVICE1-0-MIXTRIP for conveying the MIXTURETRIPLE.

Preferably, DEVICE1-1 and DEVICE1-2 are during operation in permanent fluid connection with each other and are both under PRESSURE1-1.

Preferably, DEVICE1-0 is the device that builds up PRESSURE1-1 in DEVICE1-1 and in the DEVICE1-2 against the DEVICE1-3, that is necessary to carry out REAC1-1 at TEMP1-1.

More preferably, HF and MIXTURE-TRIPLE are premixed and then are fed into DEVICE1-1.

PRESSURE1-1 can be the pressure that is needed due to the vapor pressure at the chosen TEMP1-1, PRESSURE1-1 can also be higher than the vapor pressure. Considerations for choosing a PRESSURE1-1 that is higher than the vapor pressure can for example be the requirements of DEVICE1-0. Especially when REAC1-1 is done continuously then PRESSURE1-1 is usually chosen and set to be higher than the vapor pressure.

In case of DEVICE1-1 and any DEVICE1-2 being tubes, especially coiled tubes, due to constructional limitations or due to density fluctuations and the like hot spots or cold spots can occur in spite of efforts to avoid them. Therefore any herein mentioned temperatures are meant to be average temperatures in view of possible hot or cold spots.

Conventional back pressure regulating devices, which can be used for DEVICE1-3, work discontinually, i.e. by alternating opening and closing they release the product stream while holding the pressure. This leads naturally to variations in the pressure. In view of these possible variations of PRESSURE1-1 any pressure mentioned herein is meant to be an average pressure.

All parts in contact with the mixture of HF and MIXTURE-TRIPLE and with the reaction mixture resulting from REAC1-1 are made out of respective materials which are resistant to the attack of the chemicals under the respective conditions, i.e, stainless steel, hastelloy, such as hastelloy B or hastelloy C, titanium, tantalum, silicon carbide, silicon nitride etc., they can also be passivized or lined with material inert to the chemicals, such as PTFE.

Compound of formula (I) can be used from DEVICE1-3. Preferably any gaseous components are separated from compound of formula (I). This separation is preferably clone in DEVICE1-4. Therefore compound of formula (I) can be used from DEVICE1-3 or from DEVICE1-4 for any subsequent reaction, preferably without further purification. The product from DEVICE1-3 or from DEVICE1-4 can be subjected to a further purification, preferably, the liquid phase obtained from DEVICE1-3 or from DEVICE1-4 is further purified by removing any residual low boiling residues, preferably this is done by using a film evaporator, wiped film evaporator, falling film evaporation, distillation, rectification, flash distillation or short path distillation; more preferably a wiped film evaporator.

Preferably, MIXTURE-TRIPLE is prepared in a step STEP0;
STEP0 is done before STEP1;
STEP0 comprises a reaction REAC0-1;
REAC0-1 is a reaction of compound of formula (III) with compound of formula (IV).

Preferably, the molar amount of compound of formula (IV) in REAC0-1 is from 0.5 to 1.5 fold, more preferably from 0.75 to 1.25 fold, even more preferably from 0.85 to 1.15 fold, of the molar amount of compound of formula (III).

Preferably, REAC0-1 is done at a temperature TEMP0-1, TEMP0-1 is from 180 to 300° C., more preferably from 190 to 280° C., even more preferably from 200 to 260° C., especially from 210 to 255° C., more especially from 220 to 255° C.

Preferably, REAC0-1 is done in a time TIME0-1, TIME0-1 is from 0.5 sec to 4 h, more preferably from 1 sec to 2 h, even more preferably 1 min to 1 h, especially from 2 min to 30 min, more especially from 2 min to 20 min, even more especially from 3 min to 17 min.

REAC0-1 is done at a pressure PRESSURE0-1, preferably, PRESSURE0-1 is from 10 to 1000 bar, more preferably from 20 to 600 bar, even more preferably from 50 to 500 bar, especially from 60 to 400 bar, more especially from 65 to 300 bar, even more from 65 to 200 bar, in particular from 65 to 150 bar.

Preferably, REAC0-1 is done in a continuous way.

In a preferred embodiment, STEP0 comprises one step, the step STEP0-1;
STEP0-1 comprises the reaction REAC0-1;
in STEP0-1 a mixture MIXTURE0-1 of compound of formula (III) and compound of formula (IV) is heated in DEVICE0-1 to TEMP0-1, REAC0-1 takes place in DEVICE0-1 resulting in a reaction mixture.

In another more preferred embodiment, STEP0 comprises another step STEP0-3;
STEP0-3 is done after STEP0-1;
in STEP0-3 the reaction mixture from DEVICE0-1 passes through a device DEVICE0-3, DEVICE0-3 is a device for back pressure regulation.

In another more preferred embodiment, STEP0 comprises another step STEP0-2;
STEP0-2 is done after STEP0-1 or after STEP0-3;
in STEP0-2 the reaction mixture from DEVICE0-1 or from DEVICE0-3 passes through a device DEVICE0-2, DEVICE0-2 is a device for cooling the reaction mixture;

In another preferred embodiment, STEP0 comprises all three steps STEP0-1, STEP0-2 and STEP0-3;
preferably, STEP0-2 is done after STEP0-1 and before STEP03.

Preferably, the reaction mixture is cooled by the effects of DEVICE0-2 or of DEVICE0-3 or of a combination of DEVICE0-2 and DEVICE0-3 on the reaction mixture.

Preferably, DEVICE0-1, DEVICE0-2 and DEVICE0-3 are continuously working devices.

Preferably, the method comprises another step STEP0-4, which is done after STEP0-3, in STEP0-4 the reaction mixture from DEVICE0-3 passes through a device DEVICE0-4, DEVICE0-4 is a device for separating $CO_2$ from the reaction mixture.

Preferably, the REAC0-1 is done in a tubular reactor.

Preferably, MIXTURE0-1 is fed into DEVICE0-1, during the passage through DEVICE0-1, the initially fed MIXTURE01 gradually is converted to the reaction mixture by REAC0-1.

Preferably, the reaction mixture from DEVICE0-1 is MIXTURE-TRIPLE.

Preferably, DEVICE0-1 is selected from the group consisting of tube, microreactor, shell and tube heat exchanger, plate heat exchanger and any common device which purpose is to exchange heat from a mixture;
more preferably it is a tube;
even more preferably it is a coiled tube.

Preferably, DEVICE0-2 is selected from the group consisting of tube, microreactor, shell and tube heat exchanger, plate heat exchanger and any common device which purpose is to exchange heat from a reaction mixture;
more preferably it is a tube;
even more preferably it is a coiled tube.

Especially, DEVICE0-1 and DEVICE0-2 are coiled tubes.

Preferably, DEVICE0-3 is a conventional back pressure regulating device.

Preferably, DEVICE0-4 a device capable of separating gaseous $CO_2$ from a liquid, any known device suitable for this purpose for can be used for this purpose, more preferably DEVICE0-4 is a column, a cyclone or a vessel.

The heating, preferably in DEVICE0-1, can be done be any known means, preferably it is done by electric heating or by heating with a fluid heat carrier.

Cooling in DEVICE0-2 can be done be any known means, preferably it is done by a fluid cooling medium.

Depending on the scale of the reaction and thereby on the scale of the apparatus, wherein the method is done, the cooling of the reaction mixture can be done by the effect of DEVICE0-2 on the reaction mixture, i.e. during the passage of the reaction mixture through DEVICE0-2, or it can be done by the effects of DEVICE0-3 on the reaction mixture, i.e. the passage through DEVICE0-3, contributes to the cooling. This is especially the case when the scale of the reaction is rather small, e.g. when the method is done on lab scale, whereas in case where the method is done on a production scale the cooling will usually primarily be done during the passage through DEVICE0-2.

In another embodiment, especially on production scale, cooling can also be achieved by the expansion and pressure release affected by DEVICE0-3.

Also a combination of cooling during the passage through DEVICE0-2 with a cooling by expansion affected by DEVICE0-3 is possible.

Preferably, heating in DEVICE0-1 and cooling in DEVICE0-2 is realized in form of a tube-in-tube set up, in form of a tube-in-container set up, in form of a shell and tube heat exchanger, plate heat exchanger or any common device which purpose is to exchange heat from a mixture or a reaction mixture;
more preferably, heating in DEVICE0-1 and cooling in DEVICE0-2 is realized in form of a tube-in-tube set up or in form of a tube-in-container set up.

REAC0-1 is triggered, preferably in DEVICE0-1, by the heating of MIXTURE0-1 to TEMP0-1.

The cooling in STEP0-2 is preferably done to a temperature TEMP0-2, preferably TEMP0-2 is from 0 to 180° C., more preferably from 0 to 150° C., even more preferably from 10 to 120° C., especially from 15 to 100° C., more especially from 15 to 90° C., even more especially from 15 to 85° C., in particular from 20 to 85° C.

Preferably, REAC0-1 is quenched by the cooling of the reaction mixture in DEVICE0-2 or in DEVICE0-3 or in both, preferably by cooling to TEMP0-2.

When compound of formula (2) is prepared in REAC0-1 by reaction of compound of formula (3) with chlorosulfonic acid, then the melting point of pure compound of formula (2) is ca. 35° C., therefore the lowest possible value of TEMP0-2 is governed by the conversion of the reaction, since residual compound of formula (3) and residual chlorosulfonic acid in the reaction mixture naturally lowers the melting point of the reaction mixture after the reaction and allows for lower values of TEMP0-2.

PRESSURE0-1 in DEVICE0-1 and in optional DEVICE0-2 is controlled and held by the DEVICE0-3.

TIME0-1 is the time, where MIXTURE0-1 is exposed to heating and to the TEMP0-1. During TIME0-1 the REAC0-1 takes place. TIME0-1 is therefore a residence time and when REAC0-1 takes place in DEVICE0-1, then TIME0-1 is preferably the residence time of the mixture in DEVICE0-1.

Time TIME0-2 is the time, where the reaction mixture is cooled to TEMP0-2. The cooling can be done by the action of DEVICE0-2, by the action of DEVICE0-3 or by the action of DEVICE0-2 and DEVICE0-3. The cooling quenches the reaction. TIME0-2 is therefore a residence time and is preferably the residence time of the reaction mixture in DEVICE0-2, in DEVICE0-3 or in both.

Preferably, TIME0-2 is from 0.1 sec to 2 h, more preferably from 0.5 sec to 1 h, even more preferably 1 sec to 30 min, especially from 10 sec to 30 min, more especially from 25 sec to 25 min, even more especially from 1 min to 25 min.

Preferably, TIME0-2 is from 0.0001 to 0.5 fold of time, more preferably from 0.001 to 0.3 fold, of TIME0-1.

Compound of formula (III) and compound of formula (IV) can be fed into the DEVICE0-1 as a premixed mixture or can be fed into the DEVICE0-1 separately and are mixed in DEVICE0-1.

For the purpose of mixing before or in DEVICE0-1 any suitable installation for mixing can be used, which are known in the state of the art, such as a common branch connection, e.g. a T or Y piece, or a static mixing device.

Preferably, the heating to TEMP0-1 in DEVICE0-1 is done only after compound of formula (III) and compound of formula (IV) are present as a mixture in DEVICE0-1.

The feeding of compound of formula (III) and compound of formula (IV), either separately or in form of a mixture, is done by a device DEVICE0-0.

DEVICE0-0 is a pressuring device conventionally used to convey a fluid against pressure, such as a pump. When compound of formula (III) and compound of formula (IV) are fed separately into DEVICE0-1, then preferably DEVICE0-0 has for each component a respective device, a device DEVICE0-0-COMP3 for conveying the compound of formula (III), and a device DEVICE0-0-CSA for conveying the compound of formula (IV).

Preferably, DEVICE0-1 and any DEVICE0-2 and any DEVICE0-3 are during operation in permanent fluid connection with each other and are both under PRESSURE0-1.

Preferably, DEVICE0-0 is the device that builds up the PRESSURE0-1 in DEVICE0-1 and in the DEVICE0-2 against the DEVICE0-3, which is necessary to carry out the REAC0-1 at the TEMP0-1.

More preferably, compound of formula (III) and compound of formula (IV) are mixed under ambient pressure and at ambient, temperature and then are fed into DEVICE0-1.

In case of DEVICE0-1 and/or DEVICE0-2 being tubes, especially coiled tubes, due to constructional limitations or due to density fluctuations and the like hot spots or cold spots can occur in spite of efforts to avoid them. Therefore any mentioned temperatures are meant to be average temperatures in view of possible hot or cold spots.

Conventional back pressure regulating devices, which can be used for DEVICE0-3, work usually discontinually, i.e. by opening and closing they release the product stream while holding the pressure. This leads naturally to variations in the pressure. Therefore the PRESSURE0-1 is meant to be an average pressure.

All parts in contact with MIXTURE0-1 and with the reaction mixture are made out of respective materials, which are resistant to the attack of the chemicals under the respective conditions, i.e. stainless steel, hastelloy, such as hastelloy B or hastelloy C, titanium, tantalum, silicon carbide, silicon nitride etc., they can also be passivized or lined with material inert to the chemicals, such as PTFE.

MIXTURE-TRIPLE can be used from DEVICE0-1, from DEVICE0-2, from DEVICE0-3 or from DEVICE0-4, preferably from DEVICE0-3 or from DEVICE0-4, for REAC1-1 without further purification, in case of a further purification, preferably, MIXTURE-TRIPLE, such as the liquid phase obtained from DEVICE0-4, is further purified by removing any low boiling residues, preferably this is done by using a film evaporator, wiped film evaporator, falling film evaporation, distillation, rectification, flash distillation or short path distillation; more preferably a wiped film evaporator.

In an especially preferred embodiment, REAC0-1 and REAC1-1 are done continuously and consecutively, preferably without interruption of the flow of the components; preferably DEVICE0-1 and DEVICE1-1 are connected, preferably in fluid connection, for example via DEVICE0-2.

In this case, DEVICE0-3, DEVICE0-4 and DEVICE1-0 are not mandatorily required, rather PRESSURE0-1 and PRESSURE1-1 can be identical and can be build up by DEVICE0-0 against the action of DEVICE1-3.

Depending on the dimensions and the construction of the whole apparatus setup, also DEVICE0-2 is not mandatorily required, or DEVICE0-2 can simply be realized by the device or devices, such as tubes, which connect DEVICE0-1 and DEVICE1-1.

Preferably, the reaction mixture from DEVICE0-1 or from any DEVICE0-2 can be used as MIXTURE-TRIPLE for REAC1-1;
more preferably, the reaction mixture from any DEVICE0-2 can be used as MIXTURE-TRIPLE for REAC1-1;
even more preferably, the reaction mixture from DEVICE0-1 is cooled in DEVICE0-2 to a temperature TEMP0-2 of from 120 to 210° C., preferably of from 120 to 200° C., more preferably of from 120 to 180° C.; and then the mixture from DEVICE0-2 is used as MIXTURE-TRIPLE for REAC1-1 in DEVICE1-1.

In another preferred embodiment, the reaction mixture from any DEVICE0-3 or from any DEVICE0-4 can be used as MIXTURE-TRIPLE for REAC1-1.

In another preferred embodiment, PRESSURE0-1 and PRESSURE1-1 are not identical, more preferably PRESSURE1-1 is lower than PRESSURE0-1;
more preferably the reaction mixture from a DEVICE0-3 is used as MIXTURE-TRIPLE for REAC1-1;

even more preferably the reaction mixture from a DEVICE0-4 is used as MIXTURE-TRIPLE for REAC1-1.

In case that the reaction mixture from DEVICE0-1 or from DEVICE0-2 is used directly as MIXTURE-TRIPLE for REAC1-1 any cooling after STEP0-1, preferably the cooling in STEP0-2, does not have to be as intensive as in case that the reaction mixture from REAC0-1, that is the reaction mixture from DEVICE0-1, DEVICE0-2 or from DEVICE0-3, is not used directly and immediately as MIXTURE-TRIPLE for REAC1-1, but there is some time interval in between. In this case any cooling after STEP0-1, such as the cooling in STEP0-2, should preferably ensure that the target temperature after such cooling is below the decomposition temperature of the reaction mixture obtained from REAC0-1.

EXAMPLES

Methods:

The yield of HFSI was determined by $^{19}$F-NMR using benzenesulfonylfluoride as internal reference in $D_3$-acetonitrile as solvent, if not otherwise stated Materials A mixture MIXTURE-TRIPLE-90-5-5 is prepared according to example 15 of WO2015/004220 A1. The conversion of 95% stated in this example 15 of WO2015/004220 A1 means that 5% residual CSI are present in the mixture. It is assumed that therefore the equivalent amount of chlorosulfonic acid is present in the mixture as well. Thereby MIXTURE-TRIPLE-90-5-5 contains ca. 90% of compound of formula (2), 5% of compound of formula (3) and 5% of chlorosulfonic acid, the % being % by weight based on the total weight of MIXTURE-TRIPLE-90-5-5.

A mixture MIXTURE-TRIPLE-85-7.5-7.5 is prepared according to example 5 of WO2015/004220 A1. The conversion of 92.4% stated in this example 5 of WO2015/004220 A1 means that 7.6% residual CSI are present in the mixture. It is assumed that therefore the equivalent amount of chlorosulfonic acid is present in the mixture as well. Thereby MIXTURE-TRIPLE-85-7.5-7.5 contains roughly 85% of compound of formula (2), roughly 7.5% of compound of formula (3) and roughly 7.5% of chlorosulfonic acid, the % being % by weight based on the total weight of MIXTURE-TRIPLE-85-7.5-7.5.

Example 1

The examples were carried out with
DEVICE1-0-HF: piston pump 260D from ISCO Teledyne
DEVICE1-0-MIXTRIP: piston pump 260D from ISCO Teledyne
DEVICE1-1 being a ⅛ inch coiled tube with internal volume VOLUME1 of 3.8 ml made of hastelloy C. For the heating a coiled-tube-in-container set up was used. Heating medium was conventional oil.
DEVICE1-2 being a ⅛ inch tube with ca. 1.5 mL internal volume made of hastelloy C. Cooling was done by simply contact of the tube with the air having room temperature.
DEVICE1-3: pneumatically controlled valve from SAMSON Microvalve type 3510-7 with a Cv value of 0.01.
DEVICE1-4: any gaseous components, which are essentially HCl and excess HF, were separated from the reaction mixture in a vented vessel made of stainless steel.

MIXTURE-TRIPLE-90-5-5 was fed simultaneously with HF into DEVICE1-1 at a PRESSURE1-1 of 80 bar, MIXTURE-TRIPLE-90-5-5 was fed by DEVICE1-0-MIXTRIP at a flow rate of 0.118 ml/min, and HF was fed by DEVICE1-0-HF with at a flow rate of 0.137 ml/min. TIME1-1 was approximately 15 min, TEMP1-1 was 160° C. The molar ratio of HF:MIXTURE-TRIPLE-90-5-5 resulting from the flow rates was approximately 8:1. Then the reaction mixture from DEVICE1-1 was cooled to TEMP1-2 in DEVICE1-2, TEMP1-2 was room temperature, TIME1-2 was approximately 5.9 min, and was then expanded by DEVICE1-3 into DEVICE1-4. The liquid collected was HFSI confirmed by $^{19}$F NMR. The yield was 89% based on compound of formula (2) in MIXTURE-TRIPLE-90-5-5.

Example 2

Example 1 was repeated with the sole difference, that MIXTURE-TRIPLE-90-5-5 was fed by DEVICE1-0-MIXTRIP at a flow rate of 0.198 ml/min, and HF was fed by DEVICE1-0-HF with at a flow rate of 0.057 ml/min, resulting in a molar ratio of HF:MIXTURE-TRIPLE-90-5-5 from the flow rates of approximately 2:1.

The other parameters were the same as in example 1.
The yield was 72% based on compound of formula (2) in MIXTURE-TRIPLE-90-5-5.

Example 3

The example was carried out with
DEVICE0-0: piston pump 260D from ISCO Teledyne
DEVICE1-0-HF: piston pump 260D from ISCO Teledyne
DEVICE0-1: a ⅛ inch coiled tube with internal volume VOLUME0 of 5 ml made of hastelloy C. For the heating a coiled-tube-in-container set up was used. Heating medium was conventional oil.
DEVICE1-1 being a ⅛ inch coiled tube with internal volume VOLUME1 of 3.8 ml made of hastelloy B. For the heating a coiled-tube-in-container set up was used. Heating medium was conventional oil.
DEVICE1-2 being a ⅛ inch tube with ca. 1.5 ml internal volume made of hastelloy C. Cooling was done by simply contact of the tube with the air having room temperature.
DEVICE1-3: pneumatically controlled valve from SAMSON Micro valve type 3510-7 with a Cv value of 0.01.
DEVICE1-4: a glass vessel filled with, aqueous NaOH 15 wt % for quenching purpose and for neutralizing any HCl and HF.

An equimolar mixture of CSOS and compound of formula (3) was fed by DEVICE0-0 into DEVICE0-1 at a PRESSURE0-1 of 80 bar and with a flow rate of 0.77 ml/min. TEMP0-1 of DEVICE0-1 was 230° C., TIME0-1 was approximately 5 min.

A stream of the resulting MIXTURE-TRIPLE of this example left DEVICE0-1.

A sample was taken of this MIXTURE-TRIPLE, analysis revealed a content of approximately 10.7 wt % of compound of formula (3), which means a relative ratio of the three components in this MIXTURE-TRIPLE of approximately
80% of compound of formula (2),
10% of compound of formula (3), and
10% of chlorosulfonic acid;
the % being % by weight based on the total weight of this MIXTURE-TRIPLE.

Then HF with room temperature was fed at PRESSURE1-1 of 80 bar with a flow rate of 0.24 ml/min by DEVICE1-0-HF into this stream of this MIXTURE-TRIPLE, resulting in a mixture of this MIXTURE-TRIPLE and HF, which entered DEVICE1-1, TEMP1-1 of DEVICE1-1 was 160° C., TIME1-1 was approximately 3 min. The molar ratio of HF:this MIXTURE-TRIPLE resulting from the flow rates was approximately 3:1. The reaction mixture leaving DEVICE1-1 then entered into DEVICE1-2, TEMP1-2 was room temperature. The reaction mixture leaving DEVICE1-2 was then expanded by DEVICE1-3 and then was fed into DEVICE1-4 for quenching purpose. A sample of the reaction mixture was taken between DEVICE1-3 and DEVICE1-4, the sample was mixed with water (1 part by weight of sample with 9 parts by weight of water) and analyzed by $^{19}F$ NMR which confirmed that it was HFSI.

The yield was 70% based on compound of formula (3).

Example 4

Example 1 was repeated with the differences:
MIXTURE-TRIPLE-90-5-5 was fed by DEVICE1-0-MIXTRIP at a flow rate of 1.07 ml/min.
HF was fed by DEVICE1-0-HF with at a flow rate of 0.46 ml/min.
TIME1-1 was approximately 2.5 min.
The molar ratio of HF:MIXTURE-TRIPLE-90-5-5 resulting from the flow rates was approximately 3:1.
TIME1-2 was approximately 1.5 min.
The yield was 90% based on compound of formula (2) in MIXTURE-TRIPLE-90-5-5.

Example 5

Example 1 was repeated with the differences:
MIXTURE-TRIPLE-85-7.5-7.5 was fed by DEVICE1-0-MIXTRIP at a flow rate of 1.22 g/min.
HF was fed by DEVICE1-0-HF with at a flow rate of 0.18 g/min.
TIME1-1 was approximately 5 min.
The molar ratio of HF:MIXTURE-TRIPLE-85-7.5-7.5 resulting from the flow rates was approximately 1.9:1.
Under these conditions HFSI was produced.
Yield 61.6%

Example 6

234.9 g HFSI, prepared according to example 5, was added to a solution of water (373 g) and TEA (285.2 g) while maintaining a temperature of 10 to 20° C. Then the pH value was adjusted to 9 by addition of TEA (125.6 g). Then the mixture was extracted with VN (2 times with 140 g each). The organic layers were combined (475.68 g, 21.69 wt % HFSI, determined by quantitative $^{19}F$-NMR in ACN) and were extracted with water (2 times with 153.6 g each) at 25° C. $NH_3$ (3.91 g) was added to the organic layer whereby again an aqueous layer was formed which was separated and discarded. Then aqueous LiOH (95.81 g, ca. 12.5 wt %, prepared from LiOH×$H_2O$ "battery grade" and water) was added to the organic layer, the aqueous layer that was formed was separated and discarded and then aqueous LiOH (95.61 g, ca. 12.5 wt %, prepared from LiOH×$H_2O$ "battery grade" and water) was added. The aqueous layer was again separated and discarded. Obtained was a solution of LiFSI in VN/TEA (414.83 g).

The solution was concentrated under vacuo (30 mbar) at 60° C. and filtered to provide a solution of LIFSI (140.22 g, 36.71 wt %). Then this solution of LiFSI was distilled under vacuo (ca. 7 mbar) at 60° C. During the distillation DCB (543 g) was continuously added and at the same time distillate (467 g) was collected, while maintaining approximately always the same volume in the distillation vessel. After the addition of DCB was completed, crystals had formed and were collected by filtration and washed with DCM (2 times with 50 g each). The crystals were dried under vacuo at 60° C. LiFSI (40.23 g) was obtained as white solid.

Comparative Example (i)

Of example 10 of U.S. Pat. No. 7,919,629 B2, the experiment with 2 h at 130° C. was repeated.
The yield was 55%, which is the same yield as reported by Michot in that experiment.

Example 7

The Comparative Example (i) was repeated with the difference that 1 g of MIXTURE-TRIPLE-85-7.5-7.5 was used instead of the reported 1 g ClSI.
The yield was 82%, which is considerably higher than the yield of 55% obtained with ClSI in the Comparative Example (i).

Examples 8 to 14

Example 5 was repeated with the differences as stated in Table 1:
Under these conditions HFSI was produced.

| Example | PRESSURE1-1 [bar] | TEMP1-1 [° C.] | Yield [%] |
| --- | --- | --- | --- |
| 8 | 80 | 140 | 88 |
| 9 | 80 | 110 | 58 |
| 10 | 60 | 160 | 81 |
| 11 | 40 | 160 | 84 |
| 12 | 20 | 160 | 84 |
| 13 | 12.5 | 160 | 74 |
| 14 | 5 | 160 | 72 |

Example 15

The examples were carried out with
DEVICE1-0-HF: piston pump 260D from ISCO Teledyne
DEVICE1-0-MIXTRIP: piston pump 260D from ISCO Teledyne
DEVICE1-1 being a ¼ inch coiled tube with internal volume VOLUME1 of 32 ml made of hastelloy C. For the heating a coiled-tube-in-container set up was used. Heating medium was conventional oil.
DEVICE1-2 being a ⅛ inch tube with ca. 1.5 mL internal volume made of hastelloy C. Cooling was done by simply contact of the tube with the air having room temperature.
DEVICE1-3: pneumatically controlled valve from SAMSON Microvalve type 3510-7 with a Cv value of 0.01.
DEVICE1-4: any gaseous components, which are essentially HCl and excess HF, were separated from the reaction mixture in a vented vessel made of teflon.
MIXTURE-TRIPLE-85-7.5-7.5 was fed simultaneously with HF into DEVICE1-1 at a PRESSURE1-1 of 50 bar, MIXTURE-TRIPLE-85-7.5-7.5 was fed by DEVICE1-0-MIXTRIP at a flow rate of 4.6 ml/min, and HF was fed by DEVICE1-0-HF with at a flow rate of 1.77 ml/min. TIME1-1 was approximately 5 min, TEMP1-1 was 160° C. The molar ratio of HF:MIXTURE-TRIPLE-85-7.5-7.5 resulting from the flow rates was approximately 2.4:1. Then the reaction mixture from DEVICE1-1 was cooled to TEMP1-2 in DEVICE1-2, TEMP1-2 was room temperature, TIME1-2 was approximately 15 sec, and was then expanded by DEVICE1-3 into DEVICE1-4. The liquid collected was HFSI confirmed by $^{19}$F NMR. The yield was 89% based on compound of formula (2) in MIXTURE-TRIPLE-85-7.5-7.5.

The invention claimed is:
1. A method for the preparation of a compound of formula (I);

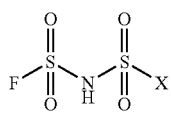
(I)

the method comprises a step STEP1;
STEP1 comprises a reaction REAC1-1;
in REAC1-1 a mixture MIXTURE-TRIPLE is reacted with HF at a temperature TEMP1-1, TEMP1-1 is at least 80° C.;
MIXTURE-TRIPLE comprises three components, a compound of formula (II), a compound of formula (III) and a compound of formula (IV);

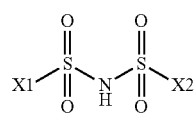
(II)

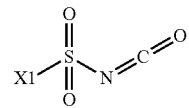
(III)

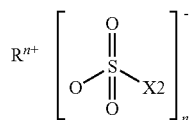
(IV)

X is identical with X1 or with X2;
X1 and X2 are identical or different and independently from each other selected from the group consisting of F, Cl, Br, I, RESF, and tolyl;
wherein RESF is a fluorinated $C_{1-9}$ alkyl, which is unsubstituted or substituted by a substituent $OCF_3$;
$R''^{n+}$ is selected from the group consisting of $H^+$, $Li^+$, $Na^+$, $K^+$, $Mg^{2+}$, $Ca^{2+}$, $Zn^{2+}$, $Cu^{2+}$, $Al^{3+}$, $Ti^{3+}$, $Fe^{2+}$, $Fe^{3+}$, $B^{3+}$,

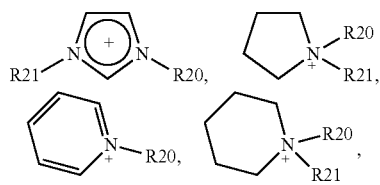

and $[N(R20)(R21)(R22)R23]^+$, and $[P(R20)(R21)(R22)R23]^+$;
R20, R21, R22 and R23 are identical or different and independently from each other selected from the group consisting of H, $C_{1-8}$ alkyl, $C_{5-6}$ cycloalkyl, phenyl, benzyl, vinyl and allyl;
n is 1, 2 or 3;
wherein
the total content of the three components in MIXTURE-TRIPLE is of from 50 to 100%, the % being % by weight based on the total weight of MIXTURE-TRIPLE;
wherein
the relative ratio of the three components in MIXTURE-TRIPLE is of from
2 to 98% of the compound of formula (II),
49 to 1% of the compound of formula (III), and
49 to 1% of the compound of formula (IV);
the % are % by weight and are based on the combined weight of the three components in MIXTURE-TRIPLE; the relative ratios of the three components add up to 100%.
2. The method according to claim 1, wherein
X1 and X2 are identical or different and independently from each other selected from the group consisting of F, Cl, Br, RESF, and tolyl;
$R''^{n+}$ is selected from the group consisting of $H^+$, $Li^+$, $Na^+$, $K^+$, $Mg^{2+}$, $Al^{3+}$,

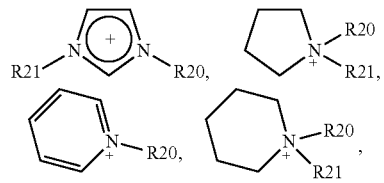

and $[N(R20)(R21)(R22)R23]^+$;
R20, R21, R22 and R23 are identical or different and independently from each other selected from the group consisting of H, $C_{1-4}$ alkyl, phenyl, benzyl, vinyl and allyl;
n is 1, 2 or 3.
3. The method according to claim 1, wherein
TEMP1-1 is from 80 to 300° C.
4. The method according to claim 1, wherein
the total content of the three components in MIXTURE-TRIPLE is of from 75 to 100%, the % being % by weight based on the total weight of MIXTURE-TRIPLE.
5. The method according to claim 1, wherein
the relative ratio of the three components in MIXTURE-TRIPLE is of from
2 to 96% of the compound of formula (II),
49 to 2% of the compound of formula (III), and
49 to 2% of the compound of formula (IV);
the % are % by weight and are based on the combined weight of the three components in MIXTURE-TRIPLE; the relative ratios of the three components add up to 100%.
6. The method according to claim 1, wherein
REAC1-1 is done in a continuous way.
7. The method according to claim 1, wherein
STEP comprises two steps, a step STEP1-1 and a step STEP1-3;
in STEP1-1 a mixture MIXTURE1-1 which is a mixture of MIXTURE-TRIPLE and HF, is heated in a device DEVICE1-1 to TEMP1-1, wherein REAC1-1 takes place in DEVICE-1 resulting in a reaction mixture, and in STEP1-3 the reaction mixture from DEVICE1-1 passes through a device DEVICE1-3, wherein DEVICE1-3 is a device for back pressure regulation.

8. The method according to claim 7, wherein
STEP1 comprises a third step, a STEP1-2, which is done between STEP1-1 and STEP1-3, in STEP1-2 the reaction mixture from DEVICE1-1 passes through a DEVICE1-2 before passing through device DEVICE1-3, DEVICE1-2 is a device for cooling the reaction mixture.

9. The method according to claim 7, wherein
the method comprises furthermore a step STEP1-4, STEP1-4 is done after STEP1-3, in STEP-4 the reaction mixture from DEVICE1-3 passes through a device DEVICE1-4, DEVICE1-4 is a device for separating gaseous components from liquid components in the reaction mixture.

10. The method according to claim 1, wherein
MIXTURE-TRIPLE is prepared in a step STEP0;
STEP0 is done before STEP1;
STEP0 comprises a reaction REAC0-1;
REAC0-1 is a reaction of the compound of formula (III) with the compound of formula (IV).

11. The method according to claim 10, wherein
REAC0-1 is done at a temperature TEMP0-1, TEMP0-1 is from 180 to 300° C.

12. The method according to claim 10, wherein
REAC0-1 is done in a continuous way.

13. The method according to claim 10, wherein
STEP0 comprises a step STEP0-1;
STEP0-1 comprises the reaction REAC0-1;
in STEP0-1 a mixture MIXTURE0-1 of the compound of formula (III) and the compound of formula (IV) is heated in a DEVICE0-1 to a TEMP0-1, REAC0-1 takes place in DEVICE0-1 resulting in a reaction mixture.

14. The method according to claim 13, wherein
STEP0 comprises another step STEP0-2;
STEP0-2 is done after STEP0-1;
in STEP0-2 the reaction mixture from DEVICE0-1 passes through a device DEVICE0-2, DEVICE0-2 is a device for cooling the reaction mixture.

15. The method according to claim 10, wherein
REAC0-1 and REAC1-1 are done continuously and consecutively.

* * * * *